(12) United States Patent
Zhao et al.

(10) Patent No.: US 10,564,105 B2
(45) Date of Patent: Feb. 18, 2020

(54) VARIABLE REDUCTION METHOD FOR SPECTRAL SEARCHING

(71) Applicant: B&W Tek LLC, Washington, DC (US)

(72) Inventors: Jun Zhao, The Woodlands, TX (US); Xin Jack Zhou, Hockessin, DE (US)

(73) Assignee: B&W TEK LLC, Washington, DC (US)

( * ) Notice: Subject to any disclaimer, the term of this patent is extended or adjusted under 35 U.S.C. 154(b) by 547 days.

(21) Appl. No.: 14/834,491

(22) Filed: Aug. 25, 2015

(65) Prior Publication Data

US 2017/0059475 A1 Mar. 2, 2017

(51) Int. Cl.
  *G01N 21/65* (2006.01)
(52) U.S. Cl.
  CPC .................... *G01N 21/65* (2013.01)
(58) Field of Classification Search
  None
  See application file for complete search history.

(56) References Cited

U.S. PATENT DOCUMENTS

| | | | | |
|---|---|---|---|---|
| 5,121,337 A | * | 6/1992 | Brown | G01N 21/274 250/339.12 |
| 6,075,594 A | * | 6/2000 | Thomas | G01J 3/28 356/328 |
| 6,317,517 B1 | * | 11/2001 | Lu | G06K 9/6228 382/115 |
| 6,584,413 B1 | * | 6/2003 | Keenan | G01J 3/28 702/194 |
| 6,675,106 B1 | * | 1/2004 | Keenan | G01J 3/28 702/194 |
| 7,072,770 B1 | * | 7/2006 | Schweitzer | G01J 3/28 702/22 |
| 7,254,501 B1 | | 8/2007 | Brown et al. | |
| 2003/0123057 A1 | * | 7/2003 | Lemmo | B01J 19/0046 356/301 |
| 2006/0161403 A1 | * | 7/2006 | Jiang | G06F 17/18 703/2 |
| 2008/0025591 A1 | * | 1/2008 | Bhanot | G06K 9/00536 382/132 |

(Continued)

OTHER PUBLICATIONS

Reinhart, When differences in significance aren't significant differences, Statistics Done Wrong (Year: 2014).*

(Continued)

*Primary Examiner* — Lina M Cordero
(74) *Attorney, Agent, or Firm* — Rimon PC

(57) ABSTRACT

A system and method for determining the composition of a sample is provided. The system and method according to the present invention comprises: obtaining one or more spectra of the sample; obtaining one or more spectra of one or more target materials; pre-process the sample and the target spectra; providing a variable reduction means that combines certain contiguous spectral variables into a single variable, wherein the intensities of the said single variable is the sum of the intensities of the said spectral variables to be combined; determining an average spectrum and the statistic distribution of the sample and/or each of the target material in the reduced dimension; determining the likelihood the sample had the same composition of each of the one or more target material; and displaying the list of the most likely target material to a user.

13 Claims, 4 Drawing Sheets

(56) References Cited

U.S. PATENT DOCUMENTS

| | | | | |
|---|---|---|---|---|
| 2009/0012723 | A1* | 1/2009 | Treado | G06F 19/703 702/28 |
| 2009/0306932 | A1* | 12/2009 | Li | G01N 21/64 702/179 |
| 2010/0158385 | A1* | 6/2010 | Jeung | G01N 23/087 382/191 |
| 2010/0191493 | A1* | 7/2010 | Brown | G01J 3/28 702/76 |
| 2010/0217537 | A1* | 8/2010 | Neiss | G01J 3/28 702/28 |
| 2013/0054603 | A1* | 2/2013 | Birdwell | G06K 9/6224 707/738 |
| 2013/0173170 | A1* | 7/2013 | Lee | G06F 19/709 702/19 |
| 2013/0197815 | A1* | 8/2013 | Gardner | G06K 9/00543 702/27 |

OTHER PUBLICATIONS

National Water Quality Laboratory Technical Memorandum (Year: 2005).*

* cited by examiner

VARIABLE REDUCTION METHOD FOR SPECTRAL SEARCHING

FIELD OF THE INVENTION

This invention generally relates to identifying materials according to their chemical composition using spectroscopic methods.

BACKGROUND

Spectral library searching is a commonly used method to identify chemical species in a sample. Traditionally, this is achieved by supplying a collection of spectra of known material, i.e. the spectral library, a spectrum of an unknown S, a searching algorithm, and a matching criterion C. The searching function $f$ compares the unknown spectrum with each of the known candidate $L_i$, in the library to calculate a matching index $P_i$, $$P_i = f(S, L_i) \quad \text{Equation 1}$$

and the candidates with matching indices above the criterion C are deemed the likely identity of the unknown.

There are a multitude of well-known search algorithms, for example, methods based on spectral correlation, Euclidean distance, least square (see S. R. Lowry, "automated Spectral Searching in Infrared, Raman and Near-Infrared spectroscopy", J. Wiley & Sons, pp 1948-1961), sum of absolute difference, and vector dot product (see J. B. Loudermilk et al, "Novel Search Algorithms for a Mid-Infrared Spectral Library of Cotton Contaminants", Applied Spectroscopy, Volume 62, Number 6, 2008).

These correlation based methods have a common shortcoming in that they do not consider the probability distribution of the spectral variables in the target materials or the sample, therefore fail to answer the question "what is the probability that the sample has the same composition as a target material".

Questions such as this fall into the domain of statistical inference, and can be addressed by performing statistical analysis of data representing the target materials and the sample. Specifically, given an observation result y of a sample, n possible candidates (targets, or target materials) and their corresponding average $\mu_i$ (i=1 to n) as well as statistical distribution $\Sigma_i$, for the hypothesis $H_i$: $y = \mu_i$, the quantity being sought is $P(H_i|y)$, i.e. the exclusive likelihood that the sample is none other than candidate i given evidence y. This is different from $P(y|H_i)$, which represents the probability of observing a result equal to or more extreme than y under the hypothesis $H_i$: $y = \mu_i$. $P(y|H_i)$ is the so called p-Value for candidate i. Bayes' theorem gives the relationship between the two:

$$P(H_i | y) = \frac{P(y | H_i) \cdot P(H_i)}{\sum_{j=1}^{n} P(y | H_j) \cdot P(H_j)} \quad \text{Equation 2}$$

where $P(H_i)$ is the prior probability of the sample being candidate i, that is, the probability without evidence y. In contrast, $P(H_i|y)$, the probability the sample being candidate i and not anything else after considering the evidence y, is called posterior probability.

The prior probability is assigned based on prior beliefs, and can be a evenly divided number, $P(H_i)=1/n$, or weighted by other properties such as material state, color, etc. Thus the key to the problem is solving for the p-Value. The data y may contain a single variable, or multiple variables, and the corresponding statistical methodology falls into the category of univariate and multivariate analysis, respectively. Univariate analysis is simple, but is based on very limited information. Spectroscopy are multivariate techniques that provide measurements of a large number of variables, therefore can provide more reliable answers. Theoretically, if the intensity distribution of the spectrum representing a target material is known, the p-Value of an observed spectrum y can be calculated. In reality, however, typical spectra contain hundreds to tens of thousands of wavelength elements, and to ascertain the distribution of such high dimensions would require an impractically large number of spectra (the so called "curse of dimensionality"). Often, it is assumed that all of these variables follow a normal distribution, hence the spectral vector follows a multivariate normal distribution. Then, with a known mean spectral vector $\mu$, and a population covariance matrix $\Sigma$, the probability density function for a measured spectral vector y of dimension q is given by $$g(t) = \frac{1}{\left(\sqrt{2\pi}\right)^q |\Sigma|^{1/2}} e^{-\frac{t}{2}} \quad \text{Equation 3}$$

$$t \equiv Z^2 = (y - \mu)^T \sum\nolimits^{-1} (y - \mu) \quad \text{Equation 4}$$

Where $\Sigma^{-1}$ and $|\Sigma|$ are the inverse matrix and determinant of $\Sigma$, respectively.

$Z^2$ is the so called Mahalanobis distance, and follows $\chi^2(q)$, a chi-squared distribution with q degrees of freedom (DoF), therefore, under the hypothesis y is a representation of the target material, the probability of getting a measured spectrum equal to or more extreme than y, i.e. the p-Value, can be calculated as the cumulative probability from $Z^2$ to $\infty$:

$$p\text{-Value} = \int_{Z^2}^{\infty} g(t) dt \quad \text{Equation 5}$$

A lower p-Value indicates a less likely occurrence.

In practice, mean spectral vector $\mu$ is estimated by $\bar{y}$, the average of n measured spectra after some normalization processes, the population covariance matrix $\Sigma$ is replaced by the sample covariance matrix S, and the quantity $$T^2 = (y - \bar{y})^T S^{-1} (y - \bar{y}) \quad \text{Equation 6}$$

follows the Hotelling distribution. The p-Value can be calculated as the cumulative probability from $T^2$ to $\infty$. The computation of $S^{-1}$ and $|S|$, however, requires S to be non-singular, which in turn requires at least q measured spectra, still a prohibitively expensive undertake. Even if such data is available, the fact that all spectra belong to the same material means that many variables are highly correlated. To those skilled in the art of linear algebra, it is obvious that such correlations among variables would make $|S|$ essentially 0, rendering the probability density function and the p-Value unstable, or indeterminable.

Therefore, it is a central problem in multivariate analysis to identify and deal with highly correlated variables. One oversimplified approach is to assume all the variables are independent, therefore all off diagonal elements of S are set to 0, and the computation of $S^{-1}$ and $|S|$ becomes straightforward. Such simplification is appropriate only if all the variables vary independently from each other, such as when variations are limited to random noises, such as signal shot noise, detector dark noise, readout noise, etc. In reality, this is rarely the case, as measurement conditions, or sample itself can impose variations that are highly correlated among certain variables. For example, in Raman spectroscopy, relative peak intensities can be affected by excitation polarization, sample focus position, sample orientation, etc. in Near Infrared spectroscopy, such variations can be induced by sample temperature, particle size, pathlength, etc. As relative peak intensity changes, intensities of wavelength elements that belong to the same peak often vary in unison. Treating such variations as uncorrelated would produce wrong p-Values. As an example, consider a simple case where a spectrum consists of 2 peaks, each covers a segment of 10 wavelength elements of equal intensities. As each one of the 10 variables within either peak is completely correlated with the other 9, they should be combined into a single variable, resulting in a total of 2 variables, each corresponding to the one peak. The Mahalanobis distance $Z^2(2)$ follows $\chi^2(2)$. However, simply treating all 20 variables as independent would result in a Mahalanobis distance $Z^2(20)=10Z^2(2)$ following $\chi^2(20)$. For $Z^2(2)=1.0$, the p-Value calculated for $\chi^2(2)$ and $\chi^2(20)$ are 0.606 and 0.968, respectively. Using a rejection criteria of $\alpha=0.05$, both p-Values pass the test. However, for $Z^2(2)=4.0$, the p-Value calculated for $\chi^2(2)$ and $\chi^2(20)$ are 0.135 (pass) and 0.0005 (fail), respectively.

Various variable reduction techniques exist that identify such correlated variables and group them together as a single component, thus reducing the dimension of the problem to a manageable level. Principal component analysis (PCA) is one such method well known to those skilled in the art of chemometric spectral analysis. In PCA, a number of spectra are acquired of a target material, the covariance matrix is used to derive m eigenvectors corresponding to the m largest eigenvalues. By linearly combining the q variables into m ($m \ll q$) mutually orthogonal principal components (PCs) that explain the majority of the variance in the covariance matrix, each original spectrum of q dimension is transformed into a new one of m dimension, represented by m scores. The covariance matrix S is reduced from $q \times q$ to $m \times m$ dimensions. Furthermore, these PCs are uncorrelated, and the new sample covariance matrix S is simplified to a diagonal matrix. The model, consisting of the average spectrum, the m PCs and eigenvalues, are then tested against any measured spectrum y to determine its p-Value, by means of calculating the new Mahalanobis distance in the score space, now called score distance (SD). However, a major drawback of PCA is that the loading of the original q variable in the PCs are heavily weighted toward the ones that exhibit large variations in the training spectra, and the wavelength regions that exhibited little change are essentially discounted. If a test spectrum happens to have extra peaks in such regions, for example due to contaminants, the p-Value will not decrease significantly, hence causing false positive errors.

Classification methods such as Soft Independent Modeling of Class Analogy (SIMCA) compensates this deficiency by considering the orthogonal distance (OD), which is the residual variance not explained by the PCA model. However, since the OD contains contribution from potentially a large number, up to (q-m) of independent variables of different magnitude, it is impossible to estimate its distribution without a large number of samples. Therefore, there is no established statistical model describing the combination of SD and OD. Pomerantsev proposed that the OD follows a $\chi^2$ distribution, and its DoF is calculated based on the mean and standard deviation of OD from a relatively small number of measurements. In practice, the DoF obtained in this way is often quite large and unstable, making the method untrustworthy.

Another problem with PCA based methods for p-Value calculation is that they can only account for spectral variations that are captured in the training data (the model). Variations outside the model but nevertheless belong to the target material would be considered outliers, resulting in false negatives. To avoid false negatives, a robust PVA model typically require the collection of a large number of spectra of the target material to capture as much variation as possible.

U.S. Pat. No. 7,254,501 B1 by C. D. Brown et al. disclosed a method that takes into account of the precision state of the unknown spectrum $\Sigma_S$, the precision state of the library spectrum $\Sigma_i$, as well as other information such as sample form, color, odor, collectively codified as $\Psi$, thereby provides a probability based matching index. However, Brown's method does not provide means of variable reduction to deal with highly correlated variables, therefore will run into problems described previously, that is, either the singularity problem of the covariance matrix S, or unreliable calculated p-Values.

What is needed, therefore, is a spectral analysis method that incorporate a variable reduction technique and can answer the question "what is the probability that the sample has the same composition as a target material". Specifically, the method shall provide means of calculating the p-Value overcoming the aforementioned problems. To be practical, such a method should not require the collection of a large number of spectral of the target material or the test sample. To be useful, it should be robust enough to handle spectral variations of the target material and the test sample, and specific enough to differentiate materials having similar but statistically different spectral signatures.

SUMMARY OF THE INVENTION

It is the goal of the present invention to provide a simple, and robust spectral analysis method that can answer the question "what is the probability that the sample has the same composition as a target material". In one form of the invention, the method comprises the steps of:

Obtaining data from a test sample, where the data comprises a measured spectrum;

Obtaining data from a number of target materials, where the data comprises a plurality of measured spectra for each target material;

For each target material,
  Providing a prior probability of the sample being the said target material;
  Providing a target specific variable reduction method that divides the spectral variables into non-overlapping segments, and combines the variables within each segment into a single variable, wherein the intensities of the said single variable is derived from the intensities of the said spectral variables to be combined;
  Calculating an average spectrum and the statistical distribution of the said target material in the reduced dimension;
  Calculating the p-Value, which is the probability of observing the sample spectrum equal to or more extreme than the measurement under the hypothesis the sample spectrum is a representation of the said target material; and
  Calculating the exclusive posterior likelihood of the sample being the said target material.

Providing a probability threshold, and listing the target materials with posterior probability above the threshold as possible candidates.

As explained before, the p-Value can be calculated using distributions such as Hotelling's $T^2$. However, the key to the calculation is reducing the spectral variables to an extent that most of the collinearities are removed. Instead of using PCA, the present invention relies on the principle that wavelength elements of the same natural feature are highly correlated, and combine them into a single element. Elements that do not contain discernable features are discarded. By combining highly correlated variables in both the target spectra and the sample spectra, the present invention overcome the singularity problem of the covariance matrix in the original dimension, therefore makes it possible to compute the p-Value using multivariate statistics. As will become evident, this is more advantageous than traditional PCA based methods because all information from the target and the sample are utilized.

As shown in Equation 2, calculating the exclusive likelihood requires the knowledge of the statistical distribution of all possible candidates. This may or may not be available. On the other hand, calculating the p-Value of a single candidate only requires that of the particular candidate. Furthermore, the role of the sample and the candidate can be reversed, that is to say, instead of testing a measured spectrum of the sample against the statistics of the target, the same can be done to test a target spectrum against the statistics of the sample, and the resulting p-Value can be used as a similarity index to identify the most likely candidate.

In another form of the invention, there is provided a method to identify the composition of a test sample, comprising the steps of:

Obtaining a plurality of spectra of the sample;
Obtaining a spectrum of each of a plurality of target materials;
For each target material,
  Providing a target specific variable reduction method that divides the spectral variables into non-overlapping segments, and combines the variables within each segment into a single variable, wherein the intensities of the said single variable is derived from the intensities of the said spectral variables to be combined;
  Calculating an average spectrum and the statistical distribution of the said sample in the reduced dimension; and
  Calculating the p-Value, which is the probability of observing the target spectrum equal to or more extreme than the measurement under the hypothesis the target spectrum is a representation of the sample, and using it as a matching index;
Providing a probability threshold, and listing the target materials with p-Value above the threshold as possible candidates.

In another form of the invention, there is provided a method to identify the composition of a test sample, comprising the steps of Obtaining one or more spectra of the test sample;
Obtaining one or more spectra of a target material;
Providing a variable reduction method that divides the spectral variables into non-overlapping segments, and combines the variables within each segment into a single variable, wherein the intensities of the said single variable is derived from the intensities of the said spectral variables to be combined;
Calculating an average spectrum and the statistical distribution of the sample and/or the target material in the reduced dimension; and Calculating the p-Value and use it as an index to either confirm or reject the hypothesis that sample and the target material have the same composition.

The methods of testing one sample spectrum against the statistics of the target spectra as well as testing one target spectrum against the statistics of the sample spectra have been described, and both belong to one-sample hypothesis testing. When the statistics of both the sample and the target are used, the method become two-sample testing, the hypothesis is that the average sample spectrum and the average target spectrum are the same. A p-Value can be calculated for the two-sample test, using for example, the two-sample Hotelling's $T^2$ distribution on the m variables, which can be easily transformed to an F-statistic, with m being the first DoF parameter.

The variable reduction method described in the invention is not limited to calculating p-Values to measure the similarity between a sample and a target. It can be used to carry out other multivariate analysis, both qualitative and quantitative. For example, all type of statistic parameters can be calculated in the reduced m dimension as opposed to the original q dimension; multivariate regression can be performed in the reduced space to quantify the chemical composition and physical properties. Alternatively, the m reduced variables can be further reduced by removing the noisy ones based on a set signal, or signal-to-noise-ratio criteria, or they can be subject to principle component analysis, partial least square, or other traditional variable reduction technique. Therefore, in another form of the invention, there is provided a method to reduce the number of variables for multivariate analysis, comprising the steps of Obtaining one or more spectra of a sample;
Providing a variable reduction method that divides the spectral variables into non-overlapping segments, and combines the variables within each segment into a single variable, wherein the intensities of the said single variable is derived from the intensities of the said spectral variables to be combined;
Performing analysis of the spectra in the reduced dimension.

The method described in the current invention can be embodied in a various forms of devices. In another form of the invention, there is provided a system to determine the composition of a sample, comprising:

Apparatus for obtaining one or more spectra of the sample;
Apparatus for providing one or more spectra of each of one or more target material;
Apparatus for pre-process the sample and the target spectra;
For each target material, apparatus for
Providing a variable reduction means that divides the spectral variables into non-overlapping segments, and combines the variables within each segment into a single variable, wherein the intensities of the said single variable is derived from the intensities of the said spectral variables to be combined;
Determining an average spectrum and the statistical distribution of the said sample and/or the target material in the reduced dimension; and
Performing multivariate analysis of the spectra of the sample and the target material in the reduced dimension to determine the probability that the sample and the target material has the same composition.

Apparatus for providing a threshold value, and displaying the list of the target materials with probabilities above the threshold as possible candidates.

The foregoing has outlined broadly the more important features of the invention to better understand the detailed description which follows, and to better understand the contribution of the present invention to the art. Before explaining at least one embodiment of the invention in detail, it is to be understood that the invention is not limited in application to the details of implementation provided in the following description or drawing figures. The invention is capable of other embodiments, and of being realized in various ways. Also, the phraseology and terminology employed in this disclosure are for purpose of description, and should not be regarded as limiting.

The advantages and features of the present invention will become apparent to those skilled in the art when read in conjunction with the accompanying following description, drawing figures, and appended claims.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 2a represents 5 spectra of a target material cyclohexane, FIG. 2b is a spectrum of a sample, ammonium sulfate, FIG. 2c is the overlaid spectra of the target material following baseline removal, smoothing, and intensity normalization. FIG. 2d is the spectrum of the sample following baseline removal, smoothing, and intensity normalization;

FIG. 3a represents an average of the 5 pre-processed spectra in FIG. 2c, FIG. 3b shows 8 spectral segments found in 3a, each one corresponding to a Raman peak of the target material, FIG. 3c is the pre-processed spectrum of the sample, and FIG. 3d identifies 5 additional spectral segments, each representing a region where a Raman peak is found for the sample, but not the target material, FIG. 3e represents sum of the segments in 3b and 3d, now totaling 13, FIG. 3f shows the 5 target spectra overlaid in the reduced dimension. FIG. 3g shows the sample spectrum in the reduced dimension; FIG. 4a is a Raman spectrum of a target material, a crystalline form of xylitol, FIG. 4b represents 5 Raman spectra of a sample, FIG. 4c is a first derivative spectrum of the target spectrum 4a, normalized such that the sum of the absolute values of the intensities of all spectral elements is 1, FIG. 4d shows the 5 overlaid first derivative spectra of the sample spectra 4b following the same preprocess. FIG. 4e shows the 1 target spectrum is in the reduced dimension, FIG. 4f shows the 5 sample spectra overlaid in the reduced dimension.

Figure 1:
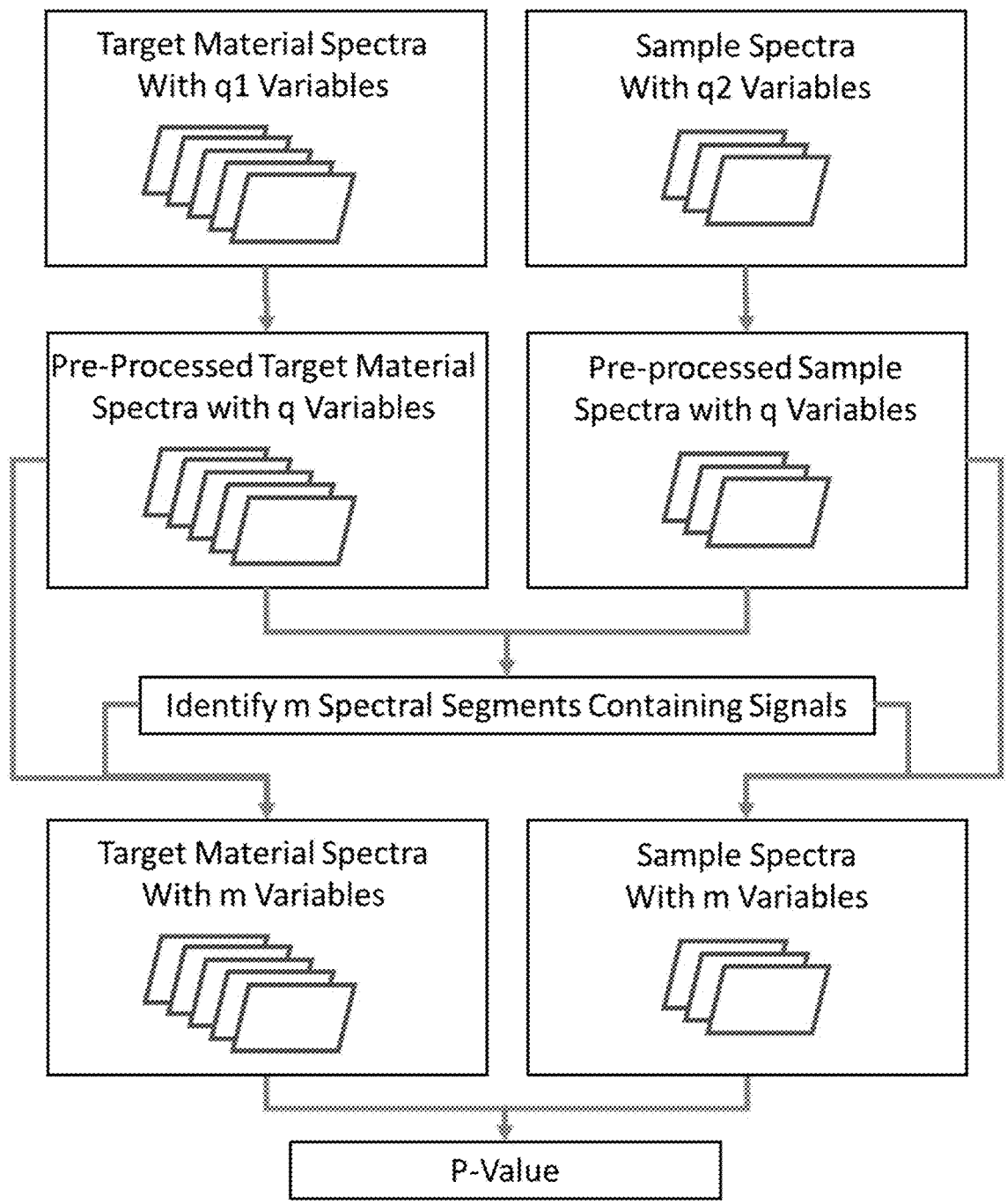
FIG. 1 illustrates the general process of variable reduction and its application in determining a spectral matching index, the p-Value.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a variable reduction system and method for spectral searching. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring to FIG. 1, The process of obtaining a p-Value starts by obtaining Nt target material spectra, each of them has q1 wavelength variables, and Ns spectra of the sample, each of them has q2 variables, where Nt and Ns are equal to or more than 1, and q2 is not necessarily the same as q1. In order for the sample and target spectra to be comparable, it is often necessary to preprocess the spectra. Such preprocessing steps are well known to those skilled in the art, and may comprise steps of interpolating the spectra to a common wavelength axis with the same q variables, correcting for intensity variations caused by instrumental response, obtaining $1^{st}$ or higher order derivative spectra, smoothing the spectral data, removing baseline, normalizing the intensities of each spectra, and any combinations of such. The pre-processed spectra are then subject to spectral analysis, the goal of which is to identify m separate segments on the wavelength axis containing unique spectral features due to the target, the sample, or both. By combining the wavelength variables in each segment into a single one, each of the target and sample spectrum is converted to a spectrum with m variables. The spectra of reduced dimension are then subject to multivariate statistical analysis to calculate the p-Value. In a one embodiment, Nt>1, Ns=1, and the multivariate statistical analysis step comprises the steps of calculating an average spectrum of the target material $\mu_t$, the covariance matrix $\Sigma$, in which all the off-diagonal elements are set to 0, and the Mahalanobis distance $Z^2$ per Equation 4. The p-Value is then determined using the $\chi^2(m)$ distribution of $Z^2$. In this embodiment, the number of target spectra Nt can be smaller than the number of reduced variables m. In an alternative embodiment, Nt>m>1, Ns=1, and the multivariate statistical analysis step comprises the steps of calculating an average spectrum of the target material $\bar{y}_t$, the covariance matrix S, and $T^2$ per Equation 6. The p-Value is then determined using the Hotelling distribution of dimension m.

The covariance matrix $\Sigma$ and S can be inflated to account for larger variations from $\bar{y}_t$ in the sample spectrum than that represented in the Nt target spectra. These two embodiments use a single sample spectrum and multiple target spectra to perform a one-sample statistical analysis. It is apparent to those skilled in the art that this can be reverse, such that multiple sample spectra and a single target spectrum are used to perform a similar one-sample statistical analysis. Alternatively, both Nt and Ns can be larger than one, and two-sample statistics can be performed to calculate a p-Value that represents the probability the average sample spectrum is the same as the average target spectrum. And finally, both Nt and Ns can be one, and the statistical distribution of the m variables for either the sample or the target material is estimated analytically, for example based on predetermined noise characteristics of the instrument, measured spectral intensities, and the data acquisition parameters.

Figure 2:
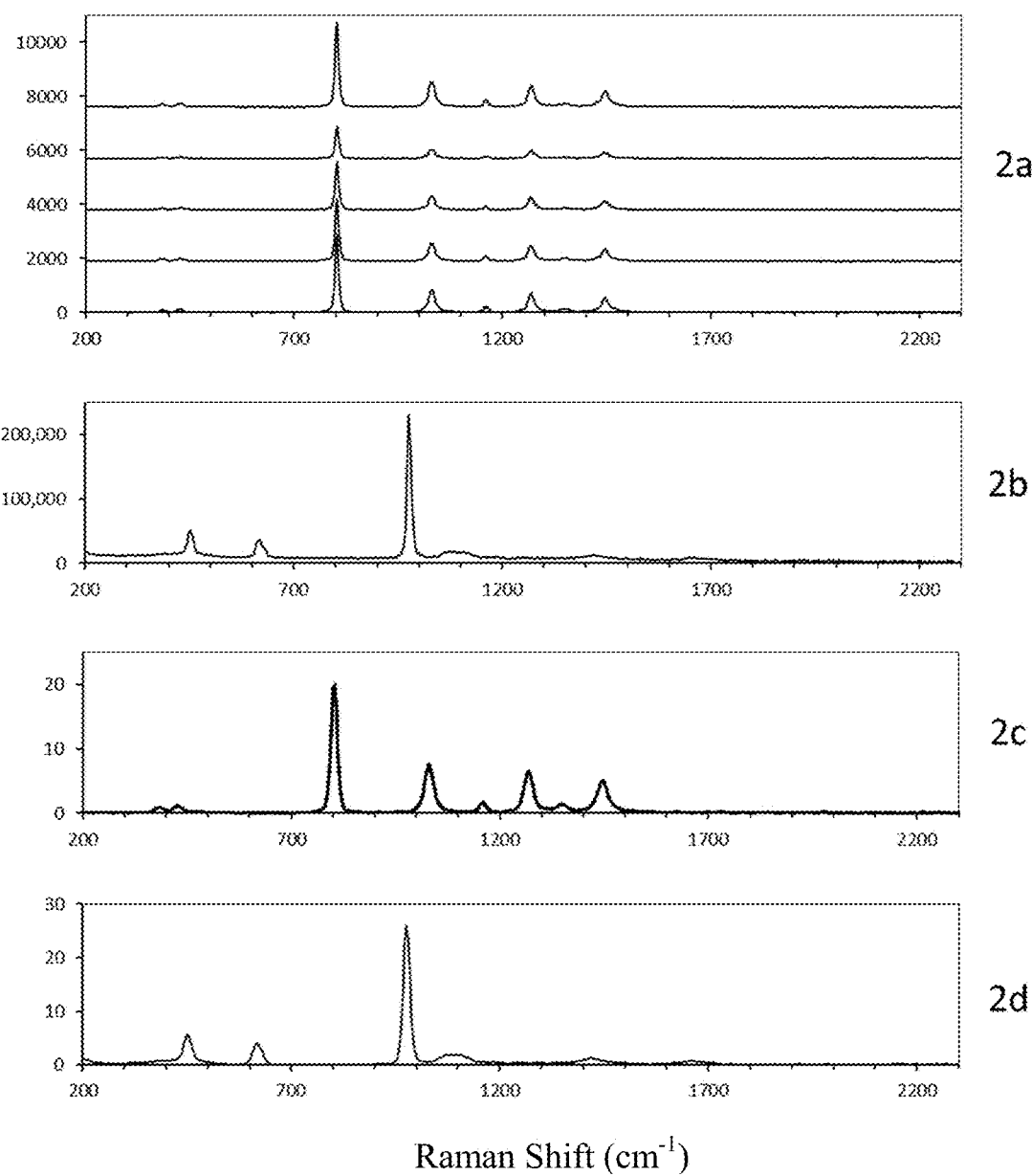
FIG. 2 illustrates the pre-processing preceding the variable reduction, where

FIG. 2 illustrates one form of the pre-process step. Shown in FIG. 2a are 5 Raman spectra of a target material, an organic solvent cyclohexane, each having 526 wavelength elements spanning a range from 200 to 2300 cm-1 Raman shift. The spectra are vertically shifted for clarity. FIG. 2b is a Raman spectrum of a sample, ammonium sulfate. Both the sample and the target spectra have been intensity corrected for instrument response variation. FIG. 2c are the same 5 target spectra, after smoothing with a Savitzky-Golay filter, subtracting a baseline, and normalizing to the same average intensity. FIG. 2d is the same sample spectrum, after similar pre-processing steps.

Figure 3:
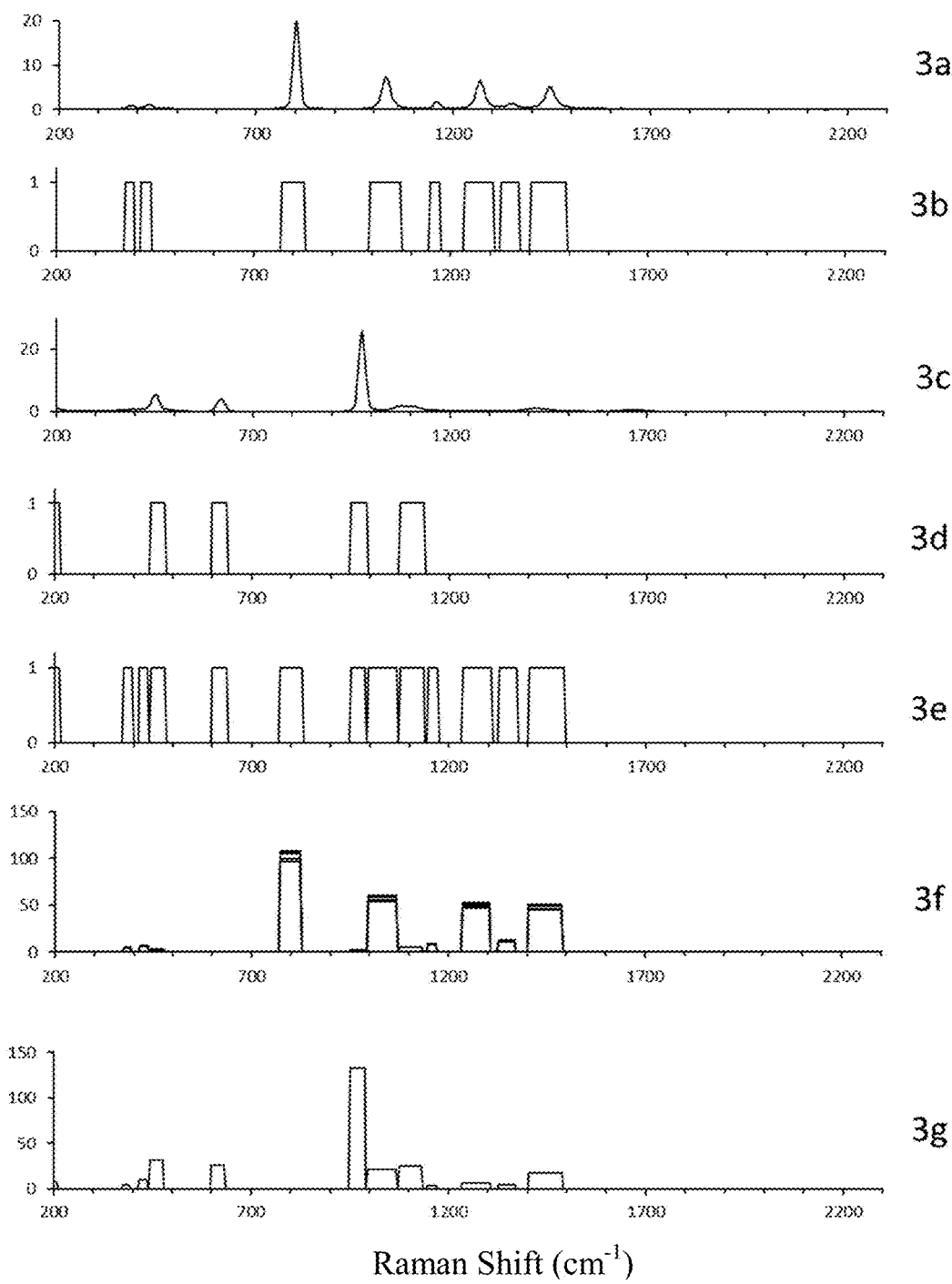
FIG. 3 illustrates the variable reduction process, where

As outlined in preceding paragraphs, the key feature of the current invention is the variable reduction step. This is important because it achieves several goals: first, it combines highly colinear variables into one, thus prevent them from skewing the result; second, the new variables are combinations of the original and are therefore more normal distributed, due to the central limit theorem; and third, it discards the regions that contains only noise, thus prevent them from diluting or even dominating the contribution from real spectral features. Depending on the forms of the pre-processed spectra, different algorithms can be used to identify the wavelength segments corresponding to the final m variables. One embodiment is illustrated in FIG. 3. FIG. 3a represents an average of the 5 pre-processed spectra in FIG. 2c. FIG. 3b shows 8 spectral segments (regions spanned by the bars with unit height) of found in 3a, each one corresponding to a Raman peak of the target material. The methods of identifying spectral peaks are well known to those skilled in the art, and are available in commercially available software packages. FIG. 3c is the same as FIG. 2d, and FIG. 3d identifies 5 additional spectral segments, each representing a region where a Raman peak is found for the sample, but not the target material. FIG. 3e represents sum of the segments in 3b and 3d, now totaling 13. Having determined the m=13 spectral segments, the intensity values within each segment are summed up for each of the 5 target spectra and 1 sample spectrum, producing 6 spectra, each having 13 wavelength variables. The 5 target spectra are overlaid in FIG. 3f, and the 1 sample spectrum in FIG. 3g, where each variable is represented by a vertical bar, with its height representing the intensity and the width corresponding to the spectral segment, wherein the width of the vertical bars are only for illustration clarity and are of no computation consequences. Thus the original 526 spectral variables are now reduced to 13 variables. Further reduction in variables can be performed, for example to remove the ones that has intensities in both target and sample spectra below a threshold.

Having obtained the spectra in reduced dimensions, the p-Value can be calculated using multivariate analysis. In this example, Nt=5, Ns=1, m=13, the Mahalanobis distance between the sample spectrum and the average target spectrum is calculated by setting the off-diagonal elements of the covariance matrix to 0. The p-Value determined using the $\chi^2(13)$ distribution is 0, meaning there is extremely low likelihood the sample has the same composition as the target material.

In this example, the intensities of each reduced variable is obtained by summing up the intensities of the original variables within the segment that is represented by the said reduced variable. This is equivalent to using integrated peak area. There are obviously countless other forms of representing the reduced variable using the intensities of the original variables within the segment, for example, using the arithmetic average, the maximum, the root mean square, the geometric average, etc.

Figure 4:
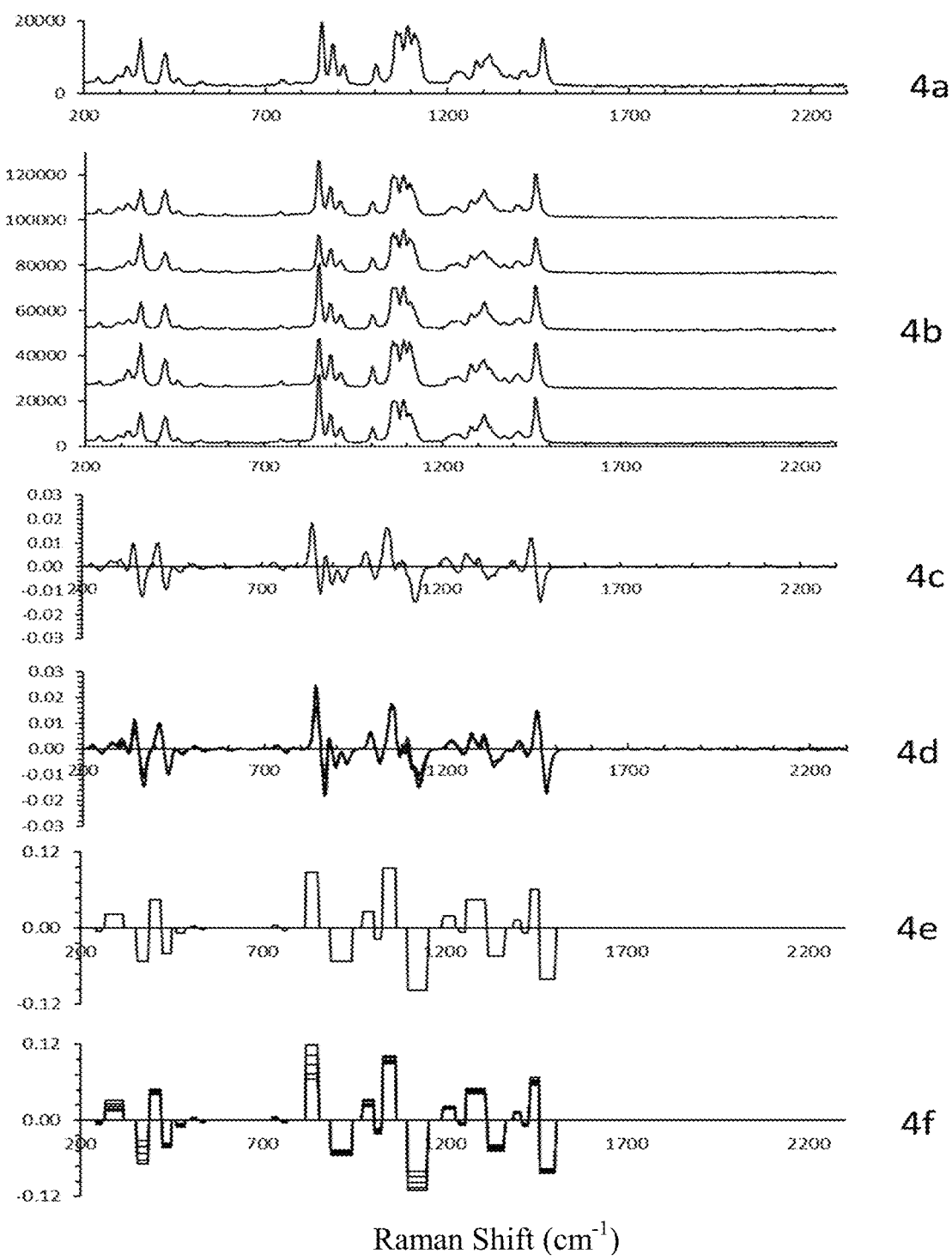
FIG. 4 illustrates the variable reduction using derivative spectra, where

FIG. 4 illustrates another form of the present invention. FIG. 4a is a Raman spectrum of a target material, a crystalline form of xylitol. FIG. 4b represents 5 Raman spectra of a sample, where the intensities are offset for clarity. FIG. 4c is a first derivative spectrum of the target spectrum 4a, normalized such that the sum of the absolute values of the intensities of all spectral elements is 1. FIG. 4d shows the 5 overlaid first derivative spectra of the sample spectra 4b following the same pre-process. Using derivative spectrum has the advantage of suppressing broad fluorescence background in Raman spectroscopy. The target spectrum and the average sample spectrum are then used to identify spectral segments. Unlike the original data which have only positive intensities, derivative spectra have both positive and negative intensities. Variable reduction in this case is achieved by first defining a signal threshold, which is set to be equal to 5% of the absolute intensity of the largest signal in the whole spectrum, and then setting all intensities whose absolute values are below the threshold. This isolates the remaining elements into segments, each containing intensities of the same sign. Each segment in the average sample spectrum corresponds to a peak and is considered a single variable. Additional segments are identified by examining the target spectrum, each representing a region where a peak is found for the target material, but not the sample. A total of 24 segments are obtained, each representing a reduced variable. The intensity values within each segment are summed up for each of the 5 sample spectra and 1 target spectrum, producing 6 spectra, each having 24 wavelength variables. The 1 target spectrum is shown in FIG. 4e, and the 5 sample spectra are overlaid in FIG. 4f, where each variable is represented by a vertical bar, with its height representing the intensity and the width corresponding to the spectral segment. Thus the original 526 spectral variables are now reduced to 24 variables. As can be seen in FIGS. 4b, 4d, and 4f, the relative spectral intensities of the sample vary significantly, thus it is likely that the variances calculated using 5 spectra underestimate the variances of the population. Therefore, the variances are inflated by a factor of 4, and the p-Value determined using the $\chi^2$ distribution is 0.95, representing a high likelihood that the target material has the same composition as the sample.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for determining a composition of a sample, the method comprising steps of:
    obtaining, from an input device, one or more sample spectra of the sample and one or more target spectra of a target, each spectrum containing q spectral variables, wherein each spectral variable has a wavelength value and an intensity value;
    calculating, by one or more processors, a representative sample spectrum by averaging the one or more sample spectra;
    calculating, by the one or more processors, a representative target spectrum by averaging the one or more target spectra;
    defining one of the representative sample spectrum and the representative target spectrum as a first representative spectrum and the other one of the representative sample spectrum and the representative target spectrum as a second representative spectrum;
    defining a first intensity threshold for the first representative spectrum and identifying m1 non-overlapping wavelength segments within which the intensity values of the spectral variables are all above the first intensity threshold for the first representative spectrum, wherein m1 is less than q;
    defining a second intensity threshold for the second representative spectrum and identifying m2 non-overlapping wavelength segments within which the intensity values of the spectral variables of the second representative spectrum are all above the second intensity threshold and the intensity values of the spectral variables of the first representative spectrum are all below the first intensity threshold, wherein m2 is less than q;
    combining the m1 non-overlapping wavelength segments in the first representative spectrum with the m2 non-overlapping wavelength segments in the second representative spectrum to obtain m non-overlapping wavelength segments, wherein m is a sum of m1 and m2, and m is less than q;
    generating, by the one or more processors, a reduced spectrum of m reduced variables from each of the one or more sample spectra and each of the one or more target spectra to obtain one or more reduced sample spectra and one or more reduced target spectra, wherein each of the m reduced variables represents one of the m wavelength segments, and its intensity value is derived from the intensity values of the spectral variables within the wavelength segment;
    performing, by the one or more processors, multivariate analysis using the one or more reduced sample spectra and the one or more reduced target spectra to determine a probability of the sample having same composition as the target, wherein the multivariate analysis using the one or more reduced sample spectra and the one or more reduced target spectra is simplified compared to multivariate analysis using the one or more sample spectra of the sample and the one or more target spectra of the target; and
    displaying, on an output device, the probability of the sample having the same composition as the target to a user.

2. The method of claim 1, wherein the intensity value of each of the m reduced variables is derived by taking a sum, an average, an average of absolute values, a root mean square, or a sum of square of the intensity values of the spectral variables within the wavelength segment.

3. The method of claim 1, further comprising a step of pre-processing the one or more sample spectra and the one or more target spectra, wherein the pre-processing step comprises steps of interpolating the one or more sample spectra and the one or more target spectra to a common wavelength axis, correcting for intensity variations caused by instrumental response, obtaining first or higher order derivatives of the one or more sample spectra and the one or more target spectra, smoothing the one or more sample spectra and the one or more target spectra, removing baseline, normalizing the intensities of the one or more sample spectra and the one or more target spectra, or a combination thereof.

4. The method of claim 1, further comprising a step of determining an average and a statistic distribution of each of the m reduced variables for the one or more reduced sample spectra and the one or more reduced target spectra.

5. The method of claim 4, wherein the statistic distribution comprises a chi squared distribution, a Hotelling distribution, a Wishart distribution, a Fisher-Snedecor distribution, or an empirical cumulative density function.

6. The method of claim 4, wherein the statistic distribution is one-sampled.

7. The method of claim 4, wherein the statistic distribution is two-sampled.

8. The method of claim 1, wherein the step of performing multivariate analysis using the one or more reduced sample spectra and the one or more reduced target spectra comprises a step of determining a p-Value, which is a probability of observing a spectrum of the sample equal to or more extreme than a spectrum of the target under a hypothesis that the spectrum of the sample is a representation of the target.

9. The method of claim 1, wherein the step of performing multivariate analysis using the one or more reduced sample spectra and the one or more reduced target spectra comprises determining a two-sampled probability that the one or more reduced sample spectra and the one or more reduced target spectra are statistically similar.

10. A system for determining a composition of a sample, the system comprising:
    a spectrometer configured to measure one or more sample spectra of the sample;
    memories configured to store one or more target spectra of a target;
    one or more processors configured to compare the one or more sample spectra of the sample and the one or more target spectra of the target to determine a probability of the sample having same composition as the target, wherein the comparison comprises a reduced-variable multivariant analysis; and
    an output device for outputting the probability of the sample having the same composition as the target determined based on the reduced-variable multivariant analysis;

wherein each spectrum comprises a set of q spectral variables with each spectral variable including a wavelength value and an intensity value, and wherein the one or more processors are configured to compare the one or more sample spectra of the sample and the one or more target spectra of the target to determine the probability of the sample having the same composition as the target by:

calculating, by the one or more processors, a representative sample spectrum by averaging the one or more sample spectra;

calculating, by the one or more processors, a representative target spectrum by averaging the one or more target spectra;

defining one of the representative sample spectrum and the representative target spectrum as a first representative spectrum and the other one of the representative sample spectrum and the representative target spectrum as a second representative spectrum;

defining a first intensity threshold for the first representative spectrum and identifying m1 non-overlapping wavelength segments within which the intensity values of the spectral variables are all above the first intensity threshold for the first representative spectrum, wherein m1 is less than q, defining a second intensity threshold for the second representative spectrum and identifying m2 non-overlapping wavelength segments within which the intensity values of the spectral variables of the second representative spectrum are all above the second intensity threshold and the intensity values of the spectral variables of the first representative spectrum are all below the first intensity threshold, wherein m2 is less than q;

combining the m1 non-overlapping wavelength segments in the first representative spectrum with the m2 non-overlapping wavelength segments in the second representative spectrum to obtain m non-overlapping wavelength segments, wherein m is a sum of m1 and m2, and m is less than q;

generating, by the one or more processors, a reduced spectrum of m reduced variables from each of the one or more sample spectra and each of the one or more target spectra to obtain one or more reduced sample spectra and one or more reduced target spectra, wherein each of the m reduced variables represents one of the m wavelength segments, and its intensity value is derived from the intensity values of the spectral variables within the wavelength segment, performing, by the one or more processors, the reduced variable multivariate analysis using the one or more reduced sample spectra and the one or more reduced target spectra to determine the probability of the sample having the same composition as the target, wherein the multivariate analysis using the one or more reduced sample spectra is simplified compared to multivariate analysis using the one or more sample spectra of the sample and the one or more target spectra of the target; and displaying, on the output device, the probability of the sample having the same composition as the target to a user.

11. The system of claim 10, wherein the one or more processors are further configured to pre-process the one or more sample spectra and the one or more target spectra, wherein the pre-processing step comprises steps of interpolating the one or more sample spectra and the one or more target spectra to a common wavelength axis, correcting for intensity variations caused by instrumental response, obtaining first or higher order derivatives of the one or more sample spectra and the one or more target spectra, smoothing the one or more sample spectra and the one or more target spectra, removing baseline, normalizing the intensities of the one or more sample spectra and the one or more target spectra, or a combination thereof.

12. The system of claim 11, wherein the performing of multivariate analysis using the one or more reduced sample spectra and the one or more reduced target spectra comprises a step of determining a p-Value, which is a probability of observing a spectrum of the sample equal to or more extreme than a spectrum of the target under a hypothesis that the spectrum of the sample is a representation of the target.

13. The system of claim 12, wherein the performing of multivariate analysis using the one or more reduced sample spectra and the one or more reduced target spectra comprises determining a two-sampled probability that the reduced sample spectra and the reduced target spectra are statistically similar.

* * * * *